US007177079B2

(12) United States Patent
Cromer et al.

(10) Patent No.: US 7,177,079 B2
(45) Date of Patent: Feb. 13, 2007

(54) METHOD AND OVERHEAD SYSTEM FOR PERFORMING A PLURALITY OF THERAPEUTIC FUNCTIONS WITHIN A ROOM

(75) Inventors: Archie E. Cromer, Harwood, MD (US); Bonnie K. Johnson, Washington, DC (US)

(73) Assignee: Virginia Tech Intellectual Properties, Inc., Blacksburg, VA (US)

( * ) Notice: Subject to any disclaimer, the term of this patent is extended or adjusted under 35 U.S.C. 154(b) by 0 days.

(21) Appl. No.: 11/084,103

(22) Filed: Mar. 21, 2005

(65) Prior Publication Data

US 2005/0162736 A1    Jul. 28, 2005

Related U.S. Application Data

(63) Continuation of application No. 10/177,673, filed on Jun. 24, 2002, now Pat. No. 6,870,673.

(60) Provisional application No. 60/299,746, filed on Jun. 22, 2001.

(51) Int. Cl.
*G03B 21/56* (2006.01)
*A61M 21/00* (2006.01)

(52) U.S. Cl. ............... 359/460; 359/451; 600/27

(58) Field of Classification Search ............ 362/1, 362/2, 24–243, 247, 404; 359/443, 450, 359/451, 460, 591–598; 600/27, 247–249; G03B 21/56; A61M 21/00; A61G 7/043
See application file for complete search history.

(56) References Cited

U.S. PATENT DOCUMENTS 1,249,500 A    12/1917 Richter (Continued)

FOREIGN PATENT DOCUMENTS

DE    631798    6/1936

(Continued)

OTHER PUBLICATIONS

Meaning of Curve, hyperdictionary, http://www.hyperdictionary.com/search.aspx?define=curve printed on Feb. 20, 2006.*

(Continued)

*Primary Examiner*—W. B. Perkey
*Assistant Examiner*—Andrew Sever
(74) *Attorney, Agent, or Firm*—Banner & Witcoff, Ltd.

(57) ABSTRACT

A system and method for providing biosynchronized therapy to a patient that creates a therapeutic environment and therapeutic stimulations that are sensitive to psychological and sensory human issues, including those particular to the patient, and that reduce psychological stress experienced by the patient so that other forms of treatment provided to the patient are enhanced and benefited. In one embodiment, the environment and stimulations can be predetermined. The therapy is applied using an overhead system that includes a suspended, multi-function that performs predetermined tasks and a lighting system, both of which provide the room with natural ambient light, artificial ambient light and predetermined task lighting. An image display system is also included for applying preselected images to the canopy over a bed of the patient. The overhead system can be used in a variety of circumstances such as a home, commercial facilities and health care facilities.

35 Claims, 10 Drawing Sheets

U.S. PATENT DOCUMENTS

| | | |
|---|---|---|
| 3,700,877 A | 10/1972 | Wilson |
| 3,769,502 A | 10/1973 | Schultz et al. |
| 4,157,584 A * | 6/1979 | Bhatt ........................ 362/479 |
| 4,213,170 A | 7/1980 | Kimball et al. |
| 4,485,599 A | 12/1984 | Perradin |
| 4,630,892 A * | 12/1986 | Howard ...................... 359/597 |
| 4,843,782 A * | 7/1989 | Gustaveson et al. ........... 52/39 |
| 4,939,582 A | 7/1990 | Holdredge et al. |
| 5,038,254 A | 8/1991 | Fabbri et al. |
| 5,064,161 A | 11/1991 | Anderson |
| 5,073,825 A | 12/1991 | Holdredge et al. |
| 5,086,375 A | 2/1992 | Fabbri et al. |
| 5,160,193 A | 11/1992 | Fabbri et al. |
| 5,188,449 A * | 2/1993 | Davis et al. ................. 362/148 |
| 5,272,608 A | 12/1993 | Engle |
| 5,293,305 A | 3/1994 | Koster |
| 5,295,051 A | 3/1994 | Cowling |
| 5,501,042 A | 3/1996 | Gustaveson et al. |
| 5,508,764 A | 4/1996 | Oles et al. |
| 5,528,425 A * | 6/1996 | Beaver ....................... 359/629 |
| 5,528,471 A | 6/1996 | Green |
| 5,676,633 A | 10/1997 | August |
| 5,681,259 A | 10/1997 | August |
| 5,708,527 A | 1/1998 | Adamson et al. |
| 5,725,472 A | 3/1998 | Weathers |
| D394,570 S | 5/1998 | Walters, III |
| 6,234,640 B1 | 5/2001 | Belfer |
| 6,254,527 B1 | 7/2001 | August |
| 6,367,934 B1 | 4/2002 | Salesky et al. |
| 6,427,389 B1 | 8/2002 | Branc et al. |
| 6,443,591 B1 * | 9/2002 | Swensson et al. .......... 362/147 |
| 6,554,433 B1 | 4/2003 | Holler |
| 6,580,559 B2 | 6/2003 | Doll et al. |
| 6,851,814 B2 * | 2/2005 | Chubb et al. .................. 362/1 |

FOREIGN PATENT DOCUMENTS

DE         3729553         3/1988

OTHER PUBLICATIONS

Light diffusion, dictionary of "The Photonics Directory", 1996-2006 Laurin Publishing.*

* cited by examiner

METHOD AND OVERHEAD SYSTEM FOR PERFORMING A PLURALITY OF THERAPEUTIC FUNCTIONS WITHIN A ROOM

CROSS-REFERENCES TO RELATED APPLICATIONS

This application is a continuation of U.S. patent application Ser. No. 10/177,673 filed Jun. 24, 2002 now U.S. Pat. No. 6,870,673, which claims benefit of U.S. Provisional Patent Application No. 60/299,746, filed on Jun. 22, 2001, under 37 CFR 1.78(a). Both applications are hereby incorporated herein by reference in their entirety.

BACKGROUND OF THE INVENTION

The present invention relates to an overhead system for performing a plurality of lighting and imaging functions within a room for the comfort, enjoyment and non-drug therapy of an occupant. More specifically, the present invention relates to an overhead canopy that cooperates with imaging and lighting systems to display images on a canopy screen, provide predetermined task lighting and diffuse ambient and artificial light deep within the room.

Health conditions force many people to spend extended periods of time in hospitals or other health care facilities. This is especially true for people who have long-term illnesses or terminal conditions. Despite the many things that hospitals have and do to make their patients comfortable, an extended stay in any hospital can be very difficult and frustrating for the patient. Staying in a hospital room and staring at the same pictures or a television over a long period of time can cause a patient to become bored, depressed and even upset. As is well known in the health care industry, an upset or irritated patient can easily turn into a bad patient. Such patients can be difficult for the hospital staff to work with and treat. Additionally, the negative mental health of these patients may hinder their own recovery.

Patients may also experience severe depression and/or anxiety if they are forced to constantly stare at plain, sterile walls and ceilings. A patient could become frustrated and outwardly aggressive and/or abusive if she is constantly deprived of the ability to view sights or events that she is accustomed to seeing. For example, a patient may become depressed if she is not able to see the sun set or the wind blow through a grove of trees. Similarly, a patient who lives at the beach may begin to resent their condition, the facility he is in and its staff if he is unable to see the ocean waves crash upon a beach.

This is even true of pediatric patients. Children who are confined to hospital rooms for even a short period of time can easily become bored and depressed. In addition, a long term hospital stay can be very difficult and possibly traumatic for a child who is unable to see or communicate with one or more of his parents, siblings, other relatives, friends and pets for extended periods of time. This is especially true for children who are quarantined or otherwise isolated from visitors and the rest of the outside world. Unfortunately, an unhappy patient may not recover as quickly as a content patient.

In order to make patients feel more comfortable while they are in the hospital, some institutions permit their patients to bring personal belongings with them and position them about the room. These belongings can include pictures, posters, etc. However, the pictures and posters are typically placed in a designated area, such as a table that is positioned to the side of the bed or at a location along one of the walls within the room. Unfortunately, over time, these pictures can be displaced because of medical procedures performed in the room. This can result in the picture being positioned too far away or in an impossible location for the patient to easily and clearly see it. Additionally, a patient may become bored with looking at the same picture for days on end. Similarly, the comforting effect of a single image/picture can diminish as the patient's stay continues. Therefore, even though a patient is able to bring at least one picture of secure and known environment or of familiar and comforting faces with him to a hospital, these pictures and posters may not prevent boredom and depression. Hence, at best, they have a diminishing, if any, beneficial effect on the patient's recovery.

In an attempt to overcome these problems, some prior art systems have tried to establish an environment within a hospital or convalescent room that would aid in the recovery of the patient. These systems provide a still picture, sound and odor. The sound and odor are related to the image on the picture. U.S. Pat. Nos. 5,676,633 and 5,681,259 to August each describe such a system for use in a health care facility or a home-based convalescent environment. Both patents to August disclose a method and system for promoting patient relaxation, reducing patient stress and expediting patient recovery by exposing the patient to external stimuli. The stimuli can be visual, auditory and/or olfactory. The patient is provided with the option of choosing one or more still, natural landscape scenes to which the patient is believed to have an innate positive (biophilic) affinity. This scene is scanned into a computer and then transferred to a flexible, high resolution fabric that is attached to the hospital curtain at the foot end of the patient's bed or the ceiling. Alternatively, the still scene can be transferred directly to a portion of the hospital curtain. The still scene can be positioned on the curtain so that it will be visible to the patient when the screen is partially closed. In addition to the visual image, the patient can be provided with natural sounds corresponding to the depicted scene and/or mild aromatic odors which are reminiscent of natural odors found in the pictured scene. As discussed above, the patient may be bored by looking at the same image for hours on end. Also, the noise and odors produced in the system may disturb other patients in the ward or in a neighboring room. Moreover, the still pictures provided cannot be changed automatically, nor can they be changed quickly. This prevents the patient from looking at different images which could sequentially depict different tropical settings, natural wonders, family members, rooms in a home, etc.

In addition to making the patient comfortable, the hospital room must also allow doctors and nurses to examine the patient and perform certain procedures. This is true of all aspects of the room including the lighting system. The lighting system in a hospital room can be critical. It must provide light for generally illuminating the room during normal times. The lighting system must also provide focused light when an examination or other medical procedure is being performed.

If the room has a window, both natural light and artificial light are available sources for illuminating the room. It is well known that natural light can aid in a patient's recovery by stimulating the production vitamin D and by maintaining or restoring the balance of the patient's circadian rhythm. However, when the sun is not facing the window, natural light rarely travels deep into the room in a direction away from the window and over the patient's bed. Also, depending on the size of the room, natural light may not travel deep into the room when the sun is facing the hospital room window. As a consequence, artificial light sources must be turned on during the day to brighten the deeper portions of certain hospital rooms. The need for artificial light during the day can aggravate or depress some patients.

Direct, natural lighting is normally not relied upon as the sole lighting source during patient examinations, drug applications or other medical tasks. Additionally, positioning the patient bed so that the natural light can be relied upon could cause the patient discomfort. For example, the sunlight could be too bright for the patient's eyes and/or too warm on the patient's body. As a result, diffusion shelves have been used to diffuse natural light as it enters a room. However, the prior art light diffusion systems do not diffuse the natural light deep enough into the room in a direction away from the windows to make them effective for completely illuminating the "dark corners" of a room—the corners furthest from the natural lighting sources (windows).

One known system for illuminating a room with diffused natural light is disclosed in German Patent No. 631,798. In this system, both natural light and artificial light are directed into a room. A reflective member is positioned along an opening for reflecting light entering the room through the opening off the ceiling. The light is then reflected off the ceiling and into the room. The depth of the diffusion into the room depends on the angle of inclination of the reflective member relative to the light source. Artificial light can also be directed at the ceiling and thereby reflected into the room. As with other prior art light diffusion systems, the entire ceiling should be painted with a very bright color that is capable of reflecting the light. Similarly, the ceiling should be substantially void of any appliances that will prevent light diffusion. Additionally, the ceiling is not shaped to force the light deep into the room in a direction away from the light source.

Additional prior art light diffusion systems are known. U.S. Pat. No. 5,293,305 to Koster discloses a light guidance system positioned along a window for illuminating the interior of a room. The light guidance system includes a light deflection device that reflects daylight coming in through the window and artificial light generated by an artificial light source located within the room. The light deflection device comprises several spaced reflectors that extend parallel to each other along the height of the window. The reflectors guide the light from the natural and artificial light sources to the room ceiling and into the room for illumination. As with other prior art illuminating systems, the system of Koster relies on the flat ceiling to direct the light into the room. Effective light diffusion cannot occur by bouncing the light of a flat ceiling because the shape of the ceiling is not capable of providing the light deep into the dark corners of the room.

The unfriendly appearance of a hospital room ceiling can also be a source of problems and frustration for a patient. For many patients, staring at a blank ceiling for an extended period of time can be another source of boredom and depression that makes them anxious and irritable. This is particularly true at night when a patient is forced to stare at ceiling having a dark, empty appearance. These problems are amplified for a pediatric patient.

Typically, young children are afraid of the dark. Therefore, a child staring into a dark, empty ceiling may become scared, begin to cry and attempt to leave his bed. While trying to escape from his bed, the child may hurt himself while tearing at any restraints holding him in the bed or any medical devices connected to his body. Such a situation can be very dangerous for a child who is connected to an intravenous fluid source. Similarly, if the child begins to cry or scream, it can be very upsetting to the other patients on the floor. Additionally, this situation can be difficult for the hospital staff because calming and comforting the child causes them additional work.

The need exists for a system that can provide different, automatically changeable images to an overhead image screen for entertaining, calming and comforting a patient so that conditions that can adversely affect the healing process, including boredom and depression, do not occur. Also, the need exists for such an overhead system that includes an artificial lighting system that provides predetermined lighting schemes within the room. Further, such a system that can effectively diffuse natural and/or artificial light deep within a room is also needed.

SUMMARY OF THE INVENTION

The present invention relates to a system that provides biosynchronized therapy to a user. Biosynchronized therapy provides a patient with a therapeutic environment and therapeutic stimulations that are sensitive to psychological and sensory human issues, including those particular to the patient, and that reduces psychological stress experienced by the patient so that other forms of treatment provided to the patient are enhanced and benefited. In one embodiment, the environment and stimulations can be predetermined. The provided benefits can include a reduction in the duration or repetition of a particular therapy, be it physical or drug based. Evidence-based mind-body research demonstrates that the psychological state (anxiety, stress) of a patient directly affects their physiological condition. These affects influence the time and effectiveness of the patient's recovery. More specifically, they influence recovery from illness, surgery or other trauma. The fields of psychoneuroimmunology and psychoneuroendocrinology have shown that body chemistry is directly influenced by numerous environmental stress conditions and stimulations. The realization that lymphoid and immune tissues are nervated, and that they contain receptors to neuropeptides whose sensitivity can be altered by hormone levels and cycles that can be controlled by the brain, along with the parallel realization that immune cells produce cytokines, steroids and peptides that influence specific and global regions of the brain has forever changed our perception of the unity of mind and body. (*IND-BODY MEDICINE: Clinician's Guide to Psychoneuroimmunology;* Churchill Livingstone; Dr. Alan Watkins; 1997) As a result, biosyncronized therapy takes advantage of the body's natural responses and enhances the effects of the therapy provided to the patient. For example, it can control the synchronizing of particular glands and the natural sacadian rhythm of the body.

The invention relates to an overhead system including a suspended canopy for use in a room, such as a hospital room, for performing multiple functions. The overhead system includes a lighting system and a canopy for providing natural ambient light, artificial ambient light and predetermined task lighting within the room. An image display system is also included for applying preselected images to the canopy over the bed of a person. The overhead system can be used in a variety of circumstances such as a home, commercial facilities and health care facilities. For example, the overhead system can be used in a pediatric hospital room to provide soft, comfortable lighting and pleasant, recognizable images for a child who is in the hospital for an extended period of time.

The system for comforting a person within a room according to one embodiment of the present invention comprises a canopy structure that extends away from a ceiling and above the person. The canopy structure has a lower outer surface that faces the room floor. The lower outer surface includes at least one light diffusion section that is shaped to diffuse light away from the canopy structure and into the room. The system also includes a lighting system that has at least one lighting source positioned within the canopy structure. The at least one lighting source is capable of projecting light in a direction away from the canopy structure for illuminating a room. An image projection screen extends along a portion of the canopy structure and receives images from an image source. The image projection screen is capable of displaying an image so that it can be viewed by the person.

In another preferred embodiment, the present invention comprises an overhead structure that extends away from a ceiling within a room. The structure includes a canopy that has a lower surface. At least a portion of the lower surface is curved so that it diffuses light from a lighting source deep into the room. An image projection screen extends along a portion of the lower surface of the canopy for displaying images received from an image projection system.

A third embodiment of the present invention includes an overhead image display structure that extends away from a ceiling of a room. The structure includes a canopy that has a curved lower surface that diffuses light into the room. The curved lower surface includes an image display screen for receiving and displaying a plurality of images provided by an image source, and a plurality of light emitting sources positioned for providing predetermined task lighting within the room. The predetermined task lighting permits a health care professional to only illuminate the portions of the patient's room that needs to be illuminated to perform a predetermined function. This prevents the patient or other people within the room from experiencing discomfort when the lights are turned on because only the lights needed to perform a function will be illuminated. This prevents overhead lights from shining in someone's eyes when the patient's legs or other parts of the body below the neck are being examined.

The images provided on the image screen can be calming to the patient and possibly stimulate his healing process. These images can be stills (individual images) or moving pictures (dynamic and continuous—like a movie). When still images are used, the image can also be automatically changed so that the person viewing them does not become bored, depressed or irritable. The images also provide the person with the opportunity to view people, pets or locations that are very important to him and that provide him great comfort or motivation for recovering quickly.

DETAILED DESCRIPTION OF THE INVENTION

Figure 1:
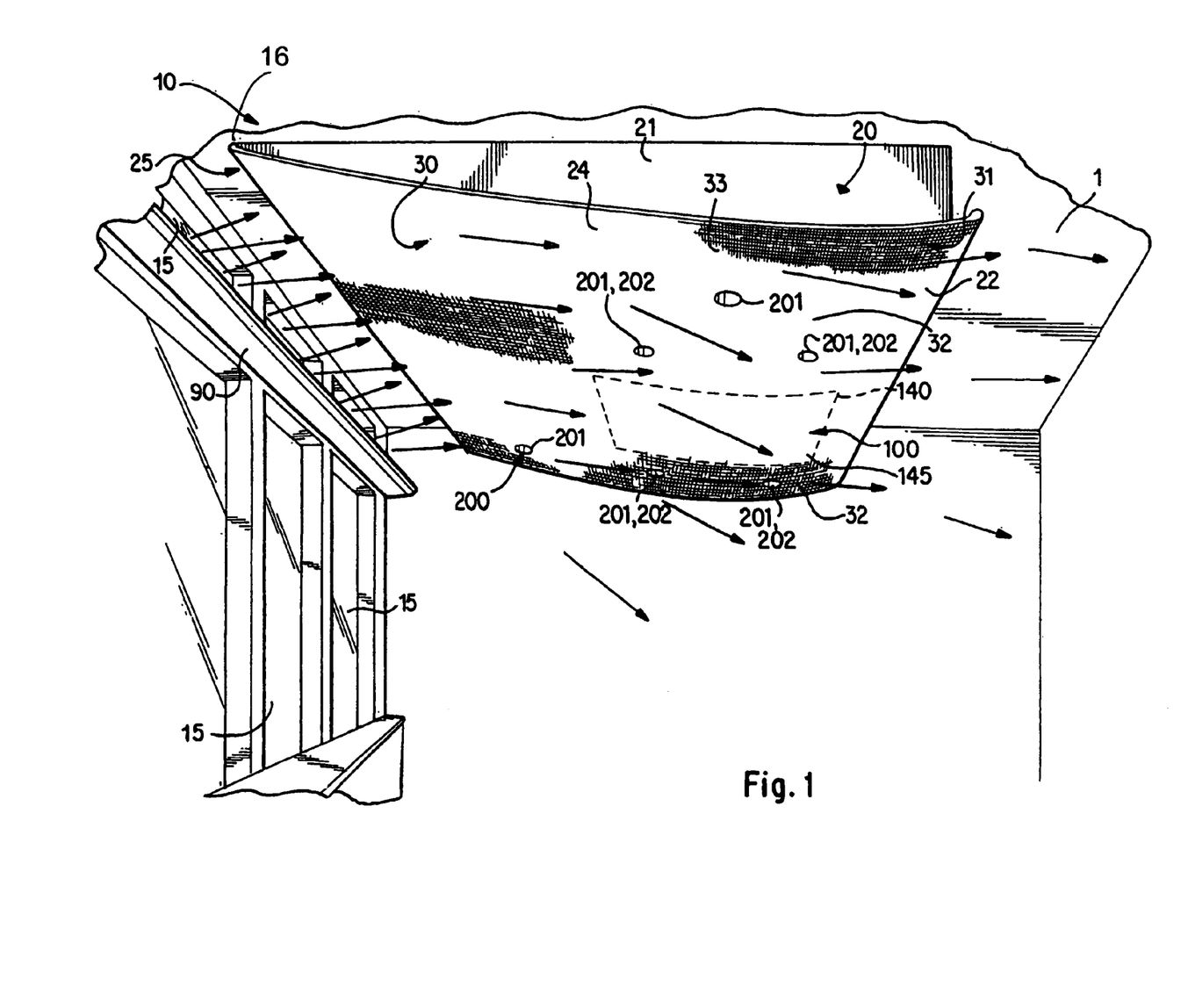
FIG. 1 is a side, perspective view of an overhead system according to the present invention with natural light being diffused deep into a room by a light diffusion member and the canopy.

As shown in FIG. 1, the present invention includes an overhead system 10 that is suspended from a ceiling 1 within a room. The overhead system 10 is used to provide therapy to a health care patient by facilitating practitioners working with known evidence-based mind-body therapy protocols, such as visualization, guided imagery or feedback. While the overhead system 10 will be described for use within a pediatric hospital room, its application is not limited to such. Instead, it can be used within any room in a hospital, convalescent home, nursing home, doctor's office, dentist's office or other health care facilities. Additionally, while not as preferred as using the overhead system 10 in a health care facility, the invention can be used outside of the health care facility, and possibly outside of the health care industry. For example, the overhead system 10 could be installed in the home of a patient who is unable to move or be moved for an extended period of time.

The overhead system 10 performs numerous functions, as discussed below. These functions include diffusing natural and artificial light deep within a room, displaying comforting, relaxing images for a viewer such as a patient and providing predetermined task lighting schemes. The overhead system 10 includes an overhead canopy 20, an image projection and display system 100 and a task lighting system 200. The overhead system 10 can also include a light diffusion member 90 that cooperates with the canopy 20 to diffuse natural and artificial light deep into the room in a direction away from windows 15 or artificial light source(s) 16.

The phrase "deep into the room" refers to light being diffused in a direction away from the windows 15, across the interior of the room and to locations proximate the side of the room opposite the windows 15 such as near or along the wall opposite the windows. Other locations that are "deep in the room" include the far or "dark" corners of the room that are away from the windows.

Figure 2:
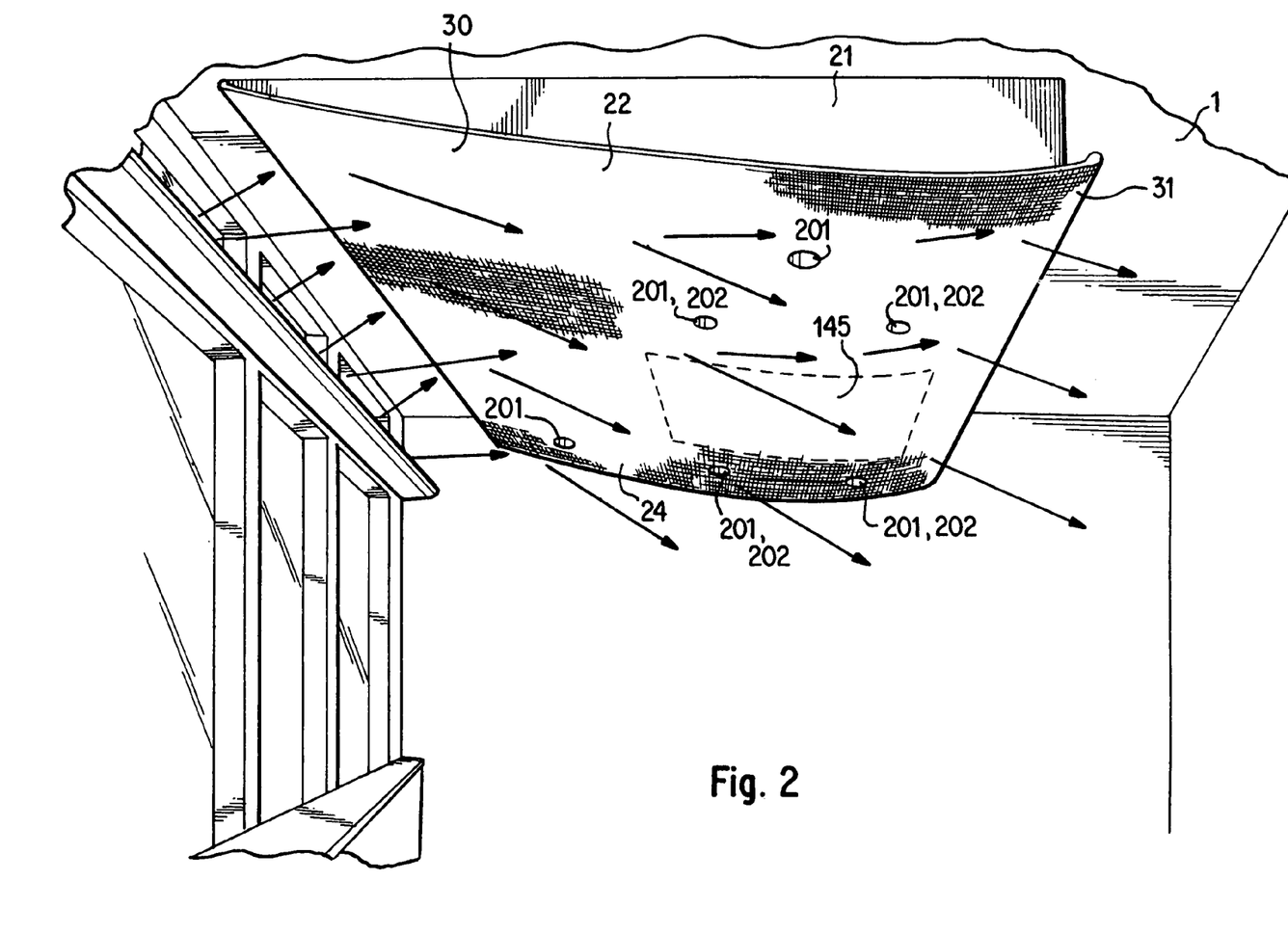
FIG. 2 is a side, perspective view of the overhead system according to the present invention with artificial light being diffused deep into a room by a light diffusion member and the canopy.
Figure 3:
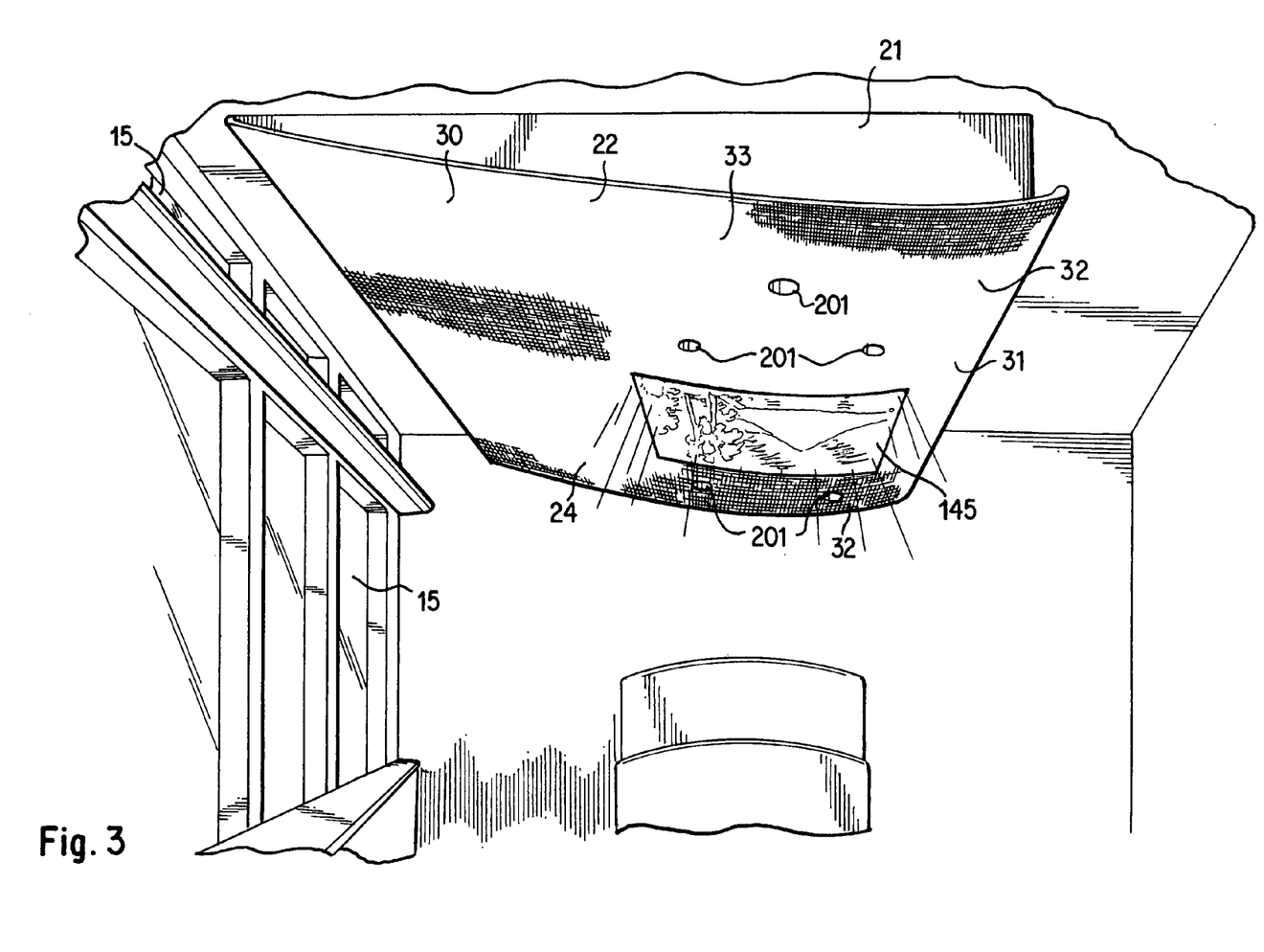
FIG. 3 is a side perspective view of the overhead system according to the present invention displaying an image on the image display screen.

FIGS. 1 and 2 illustrate the diffusion member 90 positioned along a source of natural light such as the windows 15 and a source of artificial light such as lamp(s) 16. As shown in these figures, diffusion member 90 directs the natural light that enters through windows 15 and the artificial light from source 16 inwardly and upwardly toward the canopy 20. The arrows in the figures illustrate the path that the light takes as it leaves diffusion shelf 90 and is diffused by canopy 20 deep within the room.

Figure 6A:
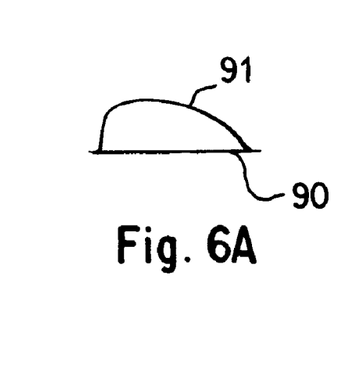
FIG. 6A is a cross section of a light diffusion member according to the present invention.
Figure 6B:
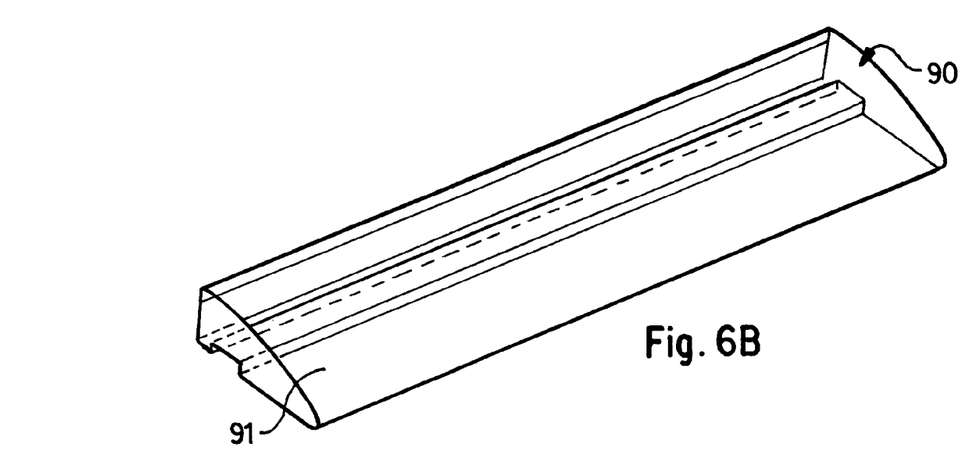
FIG. 6B is a perspective schematic view of the light diffusion member with a lower attachment groove illustrated in broken lines.
Figure 6C:
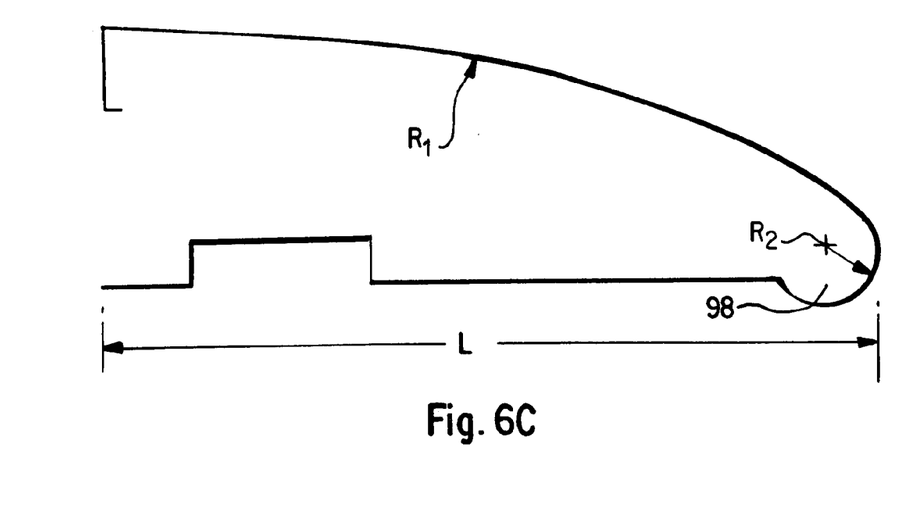
FIG. 6C is a side view of the light diffusion member shown in FIG. 6B.

As shown in FIGS. 6A–C, the diffusion member 90 is a light shelf having a convex, upper surface 91 that is curved in the direction of the interior of the room. Diffusion shelf 90 has a radius of curvature of between about 15 and 25 inches. In a preferred embodiment, the radius of curvature R1 is between about 18 and 22 inches. A preferred radius of curvature is about 19.75 inches. However, the radius of curvature can change depending on the overall size and depth of the room. The length L (depth) that the diffusion shelf 90 extends into the room can be between about 10 and 11 inches. In a preferred embodiment, the length is about 10.83 inches. The innermost point of the shelf 90 includes a rounded portion 98 having a radius of curvature R2 that is about 0.75 inch.

Figure 7:
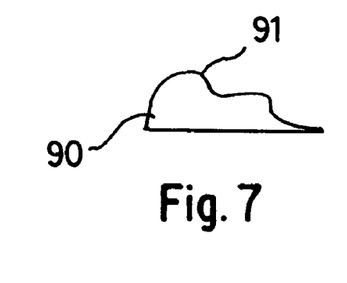
FIG. 7 is a cross section of the light diffusion member according to an alternative embodiment of the present invention.
Figure 8:
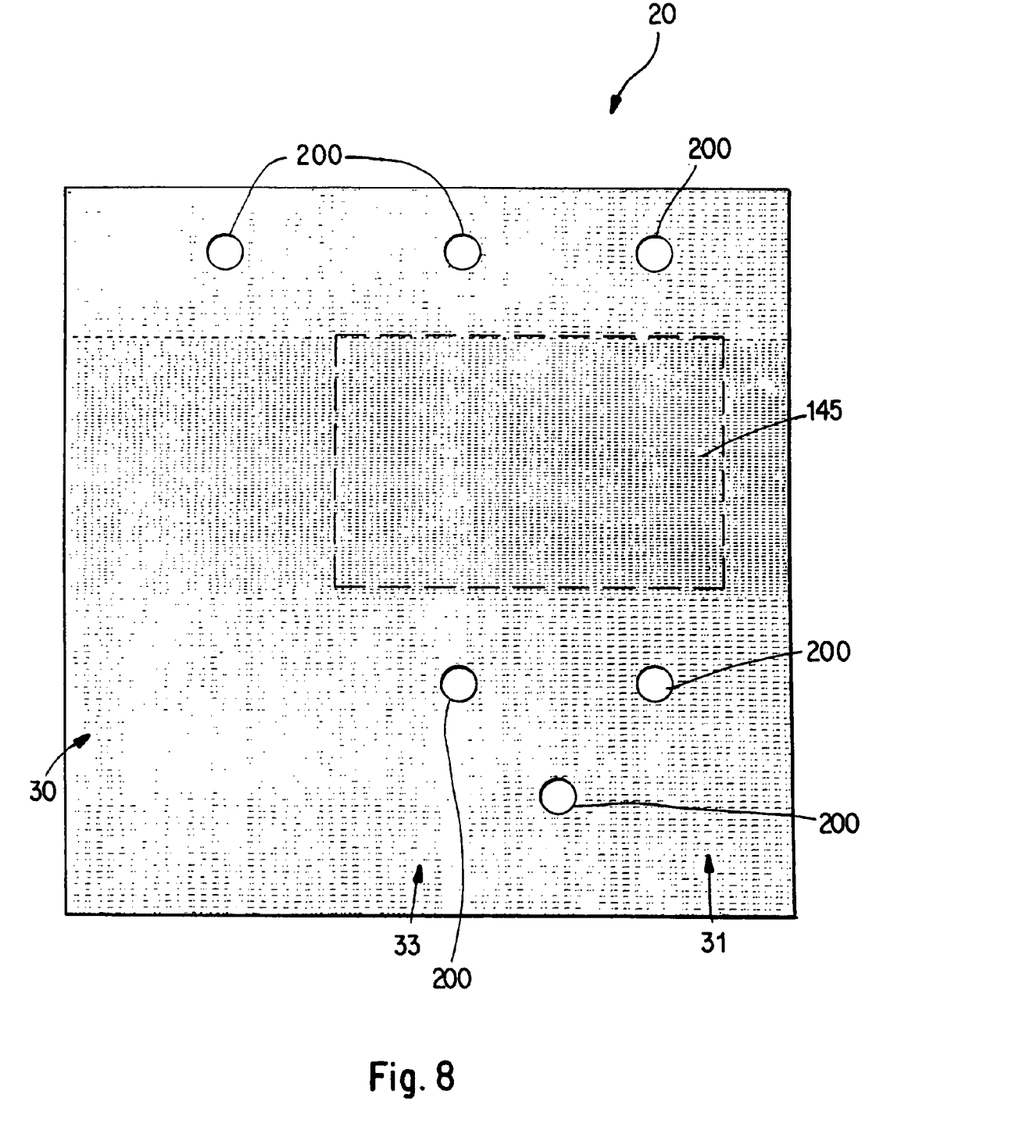
FIG. 8 is a plan view of the canopy having an alternative light source arrangement compared to that shown in FIG. 1.

In an alternative embodiment shown in FIG. 7, the upper surface 91 has multiple curves for directing the natural light at the canopy no matter the position of the sun. Other well-known shapes that efficiently diffuse light into a room could also be used for surface 91. For example, the upper surface 91 could be a flat, horizontal surface (shelf) that extends into the room. Alternatively, the upper surface 91 could extend downwardly into the room at a constant angle to the horizontal so that light can be diffused into the room. The angle could be between 1 and 30 degrees. In one embodiment, the angle of upper surface 91 is fifteen degrees relative to the horizontal.

The upper surface 91 of the diffusion shelf 90 is formed of the same rigid material as diffusion shelf 90. Alternatively, this rigid material can be covered by a fabric or other material such as a light diffusing and reflective coating or applied film surface that is capable of diffusing light in the direction of the canopy 20. Any coating or surface covering that provides at least fifty percent or higher surface reflectivity could be used. For example, a high gloss paint could be used. One such paint is sold by PPG Industries as ALK-200 L.I.C. paint, white variant 91096.

The overhead canopy 20 is secured to the ceiling 1 in a well-known manner. This includes securing the canopy 20 by screwing it into the ceiling 1 or bolting it to the ceiling 1 via brackets or other well-known securing members. Other well-known ways of securing a structure to a ceiling could also be used. When secured, the overhead canopy 20 is positioned so that it can diffuse light deep within the room and so that the patient can conveniently see the image screen 145. For example, the canopy 20 could be positioned in the middle of the ceiling 1 or centered over the patient's bed. In a preferred embodiment, the canopy 20 is positioned with the image screen 145 centered over the patient's bed.

Figure 5:
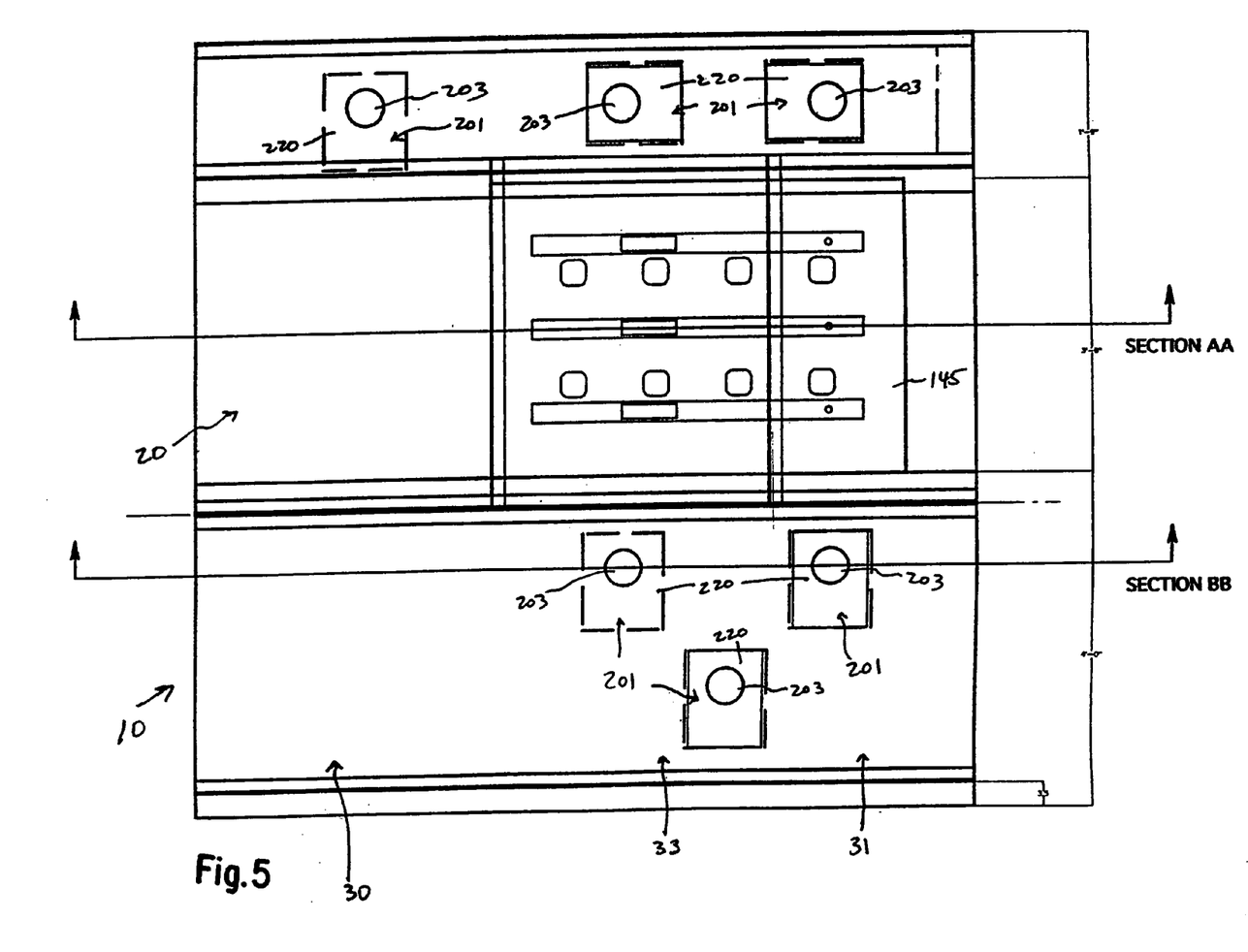
FIG. 5 is a schematic plan view of the canopy with the covering material removed.
Figure 5A:
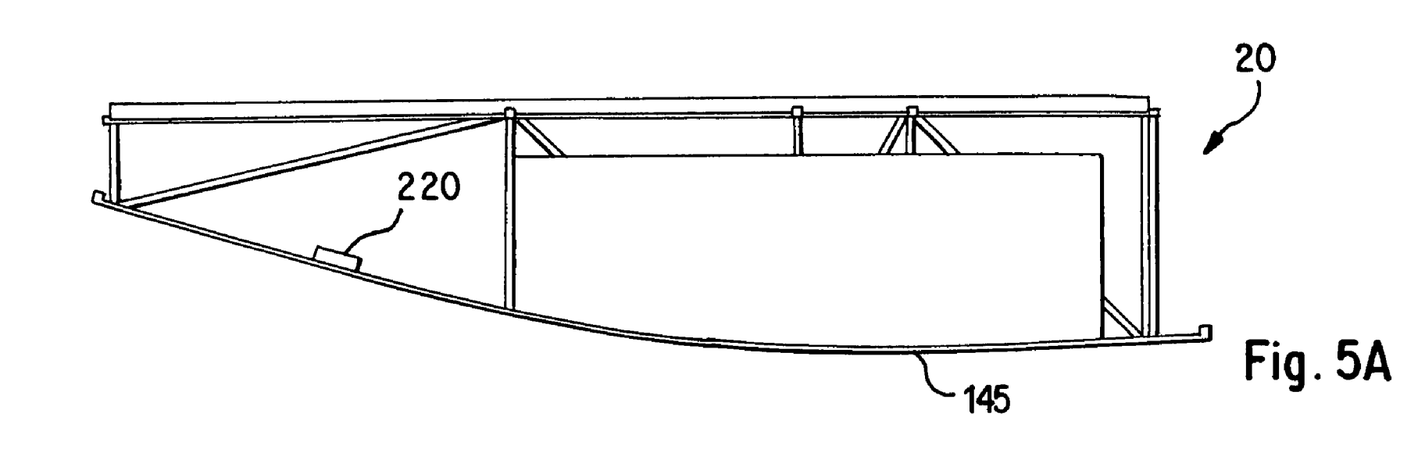
FIG. 5A is a cross section of the canopy taken along the section line AA of FIG. 5.
Figure 5B:
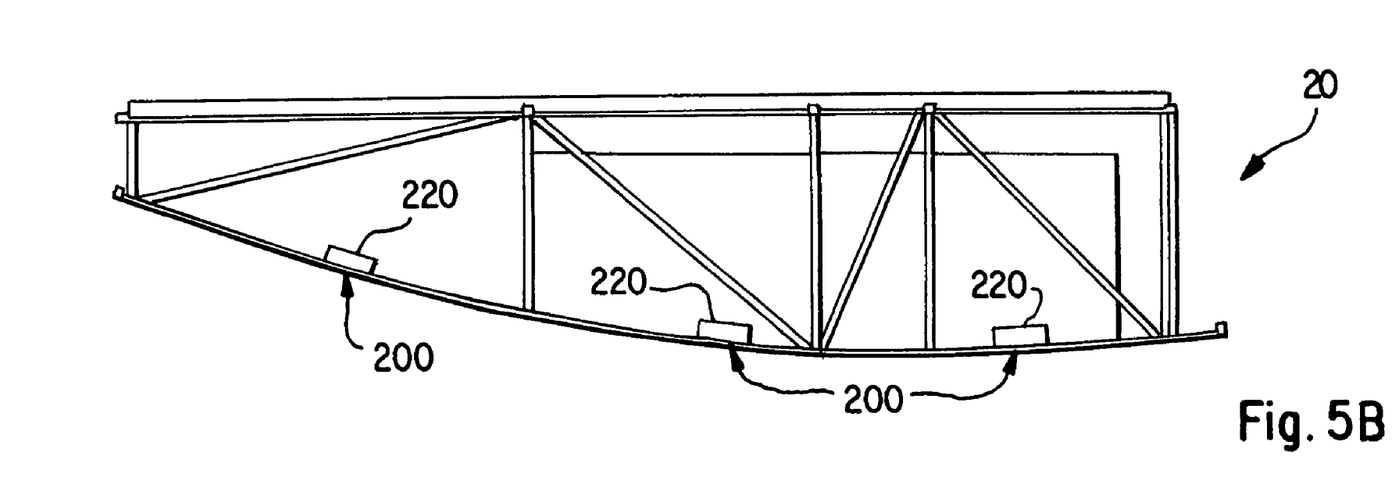
FIG. 5B is a cross section view of the canopy taken along the section line BB of FIG. 5.
Figure 5C:
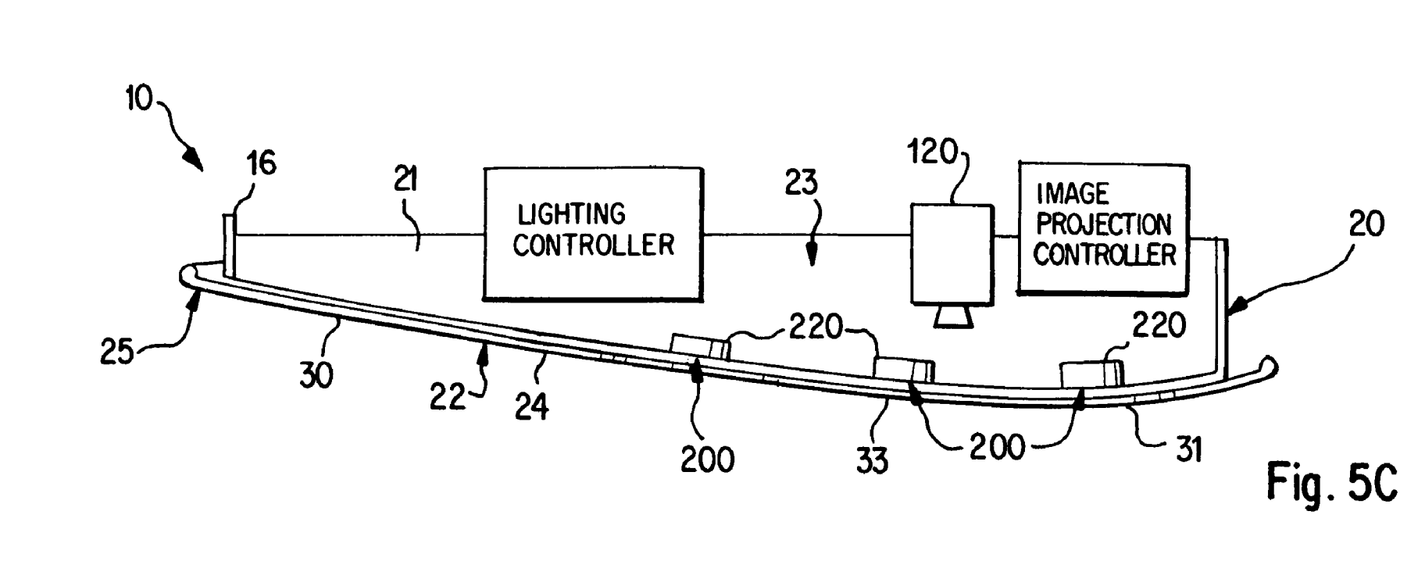
FIG. 5C is a schematic cross section of the canopy according to the present invention.

As shown in FIG. 1, the canopy 20 has vertical sidewalls 21 and a lower wall 22. The inner surfaces of the sidewalls 21 and lower wall 22 form the interior 23 of the canopy 20. As shown in FIG. 5, the interior 23 houses a plurality of the control mechanisms for the overhead system and parts of the image projection system. An endwall 25 of the canopy 20 that is proximate the windows 15 includes a mounting surface 26 for permitting artificial light from artificial light source(s) 16 to enter the room via diffusion shelf 90. The endwall 25 is oriented so that it faces toward the diffusion shelf 90 proximate the windows 15. This orientation permits light emitted from light source(s) 16 to contact diffuser 90 and be diffused in the direction of the lower wall 22 of canopy 20 and into the room. Alternatively, the mounting surface 26 could be positioned in the direction of a light diffuser 90 that is located elsewhere in the room for directing the light from source(s) 16 immediately into the room and/or off the lower wall 22.

The outer surface 24 of lower wall 22 faces into the room in order to diffuse light from both light sources 15, 16 deep into the room. As shown in FIGS. 1, 2 and 5–5C, the lower wall 22 of the canopy is curved in a first direction along a first section 30 and in a second direction along a second section 31. The curved sections 30, 31 provide a continuously angled surface that diffuses light from sources 15, 16 deep into the room as discussed below. The second, curved section 31 includes curved light diffusing areas 32 that surround an opening 140 in outer surface 24 for an image display screen 145.

Light diffusion portions of sections 30 and 31 that are primarily responsible for diffusing light into the room are covered with a material that is capable of performing this diffusing function. The light diffusion material also prevents a "dark hole" effect from being created on the ceiling when the lights in the room are turned off. In a preferred embodiment, the light diffusing material can be a surface treated perforated polypropylene. However, other materials that are capable of diffusing light that is directed at the canopy 20 deep within the room without creating a "dark hole" ceiling could also be used. These other materials include lightweight, rigid materials covered with a composite material of PVC and fiberglass, such as Hunter Douglass Sheerweaves® 2000 fabric.

Figure 9:
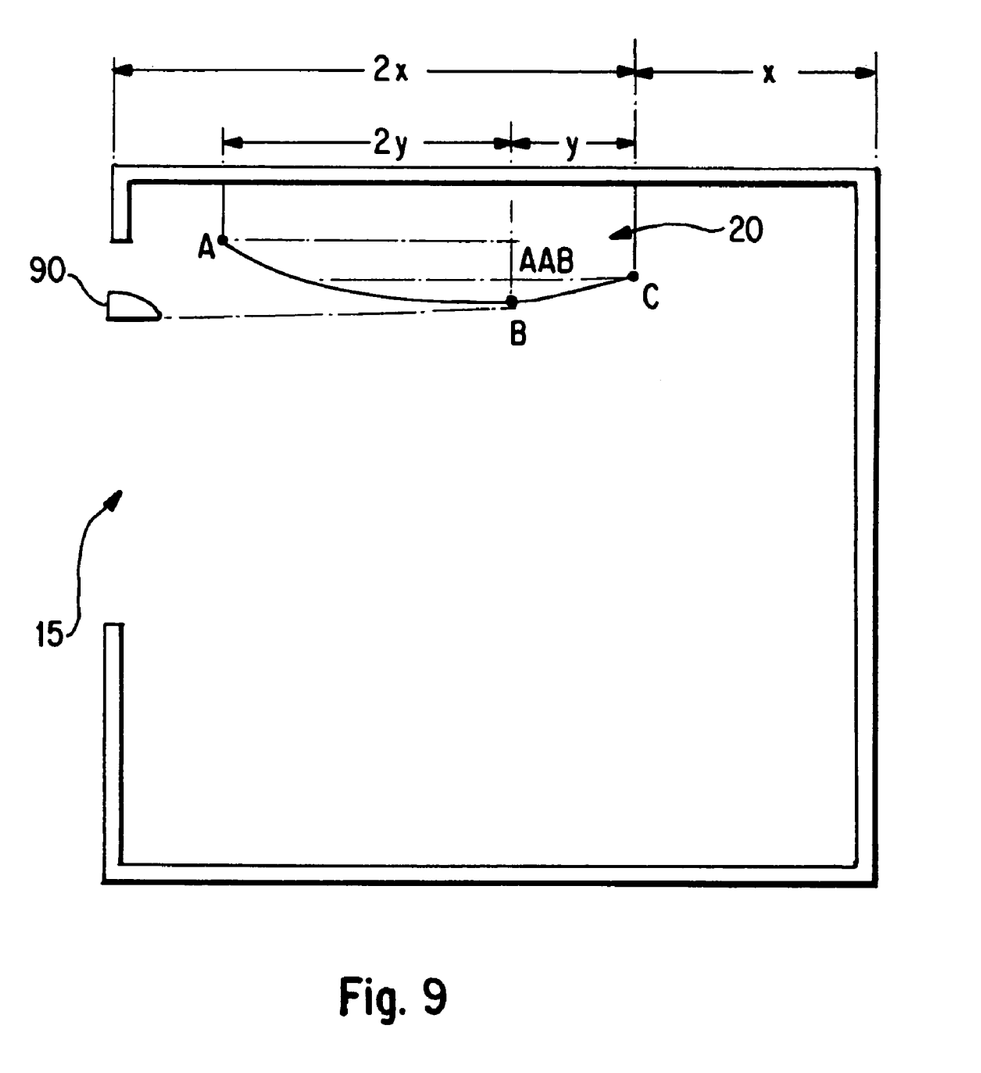
FIG. 9 is a schematic view of the canopy extending from a ceiling and a cooperating light diffusion member.

As mentioned above and as shown in FIGS. 1, 2 and 5–5C, the sections 30 and 31 are not flat like a prior art ceiling. Instead, section 30 curves downward from opening 26 near the windows 15 to the section 31 that is positioned about the middle of the room and/or over the patient's bed. Contrary to section 30, section 31 curves upwardly as it moves in a direction away from the windows 15 and section 30. The continuous curves of both sections 30, 31 provide a gradual, continuous change in the elevation of the lower wall 22 over its length. The section 30 of wall 22 has a radius of curvature of between about 15 and 23 feet. In a preferred embodiment, the radius of curvature is about 18 feet. The section 31 has a radius of curvature of between about 15 and 23 feet. In a preferred embodiment, the radius of curvature is about 18 feet. However, these radii of curvature will change as the size of the canopy 20 changes. The shape of the canopy 20 can change with the size of the exterior windows and the room depth and height. In one embodiment, the depth of the canopy is two-thirds the depth of the room as shown in FIG. 9. Therefore, the specific depth of the canopy into the room will change with the depth of the room. For example, the canopy 20 could be about six to seven feet long for a room that is ten feet deep, and twice that depth for a room that is twenty feet deep. It is also contemplated that sections 30 and 31 could be angled with a slight curve at their lower extremes.

As shown in the figures, especially FIG. 9, the curve between points A and B is about two-thirds of the canopy surface. Similarly, the curved surface between points B and C is about one-third of the canopy surface. Thus, point B is the lowest surface of the canopy and point A is the highest. This is clearly shown in the figures, especially FIGS. 5–5C and 9. Point A is typically at the same height within the room as the top of the windowsill. Point B is typically positioned so that it is no lower within the room than the leading edge of the light diffusion shelf 90. In this embodiment, the diffusion shelf is located above eyelevel for the patient. In one embodiment, the diffusion shelf is located at least six feet above the floor. Point C is positioned along the height of the canopy 20 at about the center point (half) of the vertical difference between point A and point B. As a result, point C is a function of the distance between points A and B. The circle circumscribing points A, B and C determines the radius of curvature for the canopy.

The continuous change in elevation caused by the slow, gradual slopes and opposing curves of sections 30 and 31 results in light being diffused deep into the room. These sections 30, 31 diffuse the light further into the room than a flat, conventional diffusion ceiling. The diffused light is illustrated in the figures by the depicted arrows. As shown in the figures, light can be directed to canopy 20 by the diffusion shelf 90 or it can come directly from a light source. It is not necessary to use diffusion shelf 90 for the canopy 20 of the present invention to operate properly. The slow slope of each section produces an infinite number of diffusion angles that combine with the infinite number of angles at which the light approaches the canopy 15 to cause the light from the sources 15, 16 to diffuse deep within the room. This is contrary to the prior art diffusion systems that rely on the angle of the light to dictate the direction of diffusion because the flat, planar ceilings can only diffuse light in one direction—perpendicular to the angle at which the light contacts the ceiling.

The sections 30, 31 of the canopy 20 provide an infinite number of diffusion angles. These angles cooperate with the angle of attack of the light emitted from the light source or diffusion shelf 90 to diffuse the light in multiple directions and deep within the room. When the light is diffused or otherwise directed at the curved sections 30, 31 or the transition area 33 between sections 30 and 31, it will be diffused in as many directions as there are contact angles on these sections. For example, the larger angles (measured with respect to the horizontal) that are proximate the opening 26 cause the light to be diffused over the center of the room or the patient bed. The smaller angles of section 30 and transition area 33, which are proximate section 30, will diffuse the light deeper into the room than the larger angles. Similarly, the angles of section 31 which extend in an opposite direction to those of section 30 are capable of diffusing the light to the deepest corners of the room as shown in FIGS. 1 and 2. Transition area 33 can include a flat surface that is substantially parallel to the image display screen 145 (when flat) and the floor of the room.

The image display screen 145 can be curved so that it follows the contour of lower wall 22 or it can be flat. The opening 140 is covered with a material that is different from that covering the other portions of lower wall 22. This is because the screen 145 is intended to perform a different function. Instead, the main function of the screen 145 is to display projected images. The screen 145 is also intended to diffuse light when it is not displaying an image. Accordingly, the material that forms screen 145 is chosen for its ability to clearly display an image while also being able to diffuse light deep into a room. In a preferred embodiment, the screen 145 includes a translucent material covered by a vinyl covered cotton fabric, such as Hunter Douglas "PIMA", a 100% cotton fabric with a vinyl coating. Like PIMA, the materials for the screen 145 are light filtering and fade and stain resistant materials. The materials used for the screen 145 can include a small weave pattern that does not affect the clarity of the projected image. Also, the translucent material and covering fabric cooperate to diffuse light and to prevent the canopy from appearing dark when an image is not being projected. In an alternative embodiment, the screen 145 of the preferred embodiment of the present invention includes an array of pixels for presenting images that represent computer text and graphics, television signals or video feeds. Additionally, the screen 145 could be the same as the material used to cover sections 30, 31. In this embodiment, the fabric would be stretched taught as a screen for use with an image projection system, such as a Kodak DP1100 Digital projector.

The present invention also includes an image projection system 100 for providing an image on the image display screen 145 of canopy 20. The image is intended to make the patients feel more secure and comfortable so that they will remain in good spirits. As discussed above, a happy patient can recover quicker and be less of a drain on the hospital staff. Additionally, comfortable and occupied pediatric patients are less likely to injure themselves by trying to escape restraints or remove needles in order to escape their beds.

Although this specification may refer to the invention or components of the invention as relating to "video," "screens," "projected" images, etc., any manner of displaying images onto a screen or surface is adaptable for use with the invention. Specifically, although the invention is referred to as an "image projection system" or an "image source", this term is intended to indicate that either still or moving images are displayed by projection or direct display. This phrase does not limit the invention to projected slides, video or video related display mechanisms. Further, any type of images may be displayed on the screen(s) of the present invention including still images (i.e., "slides"), arbitrary light patterns as from prism refraction, color filters, shadowing, etc. In addition, the images could be stored analog or digital images from a stored file such as a video tape, a DVD or other well known source that store multiple images such as movies. A digital camera providing a recorded or live feed could also be used as the image source.

In a preferred embodiment, the images can include transparencies, still photographs, multiple stored images on a roll or conventional slides of anything that is pleasant or comforting to the patient, such as his/her relatives, the sky with different cloud formations, trees, flowers, etc. In one such embodiment, backlit photographic transparencies are used to apply an image to the image display portion (screen 145) of the canopy. The transparencies can be either a single image or multiple images on a roll. An electronic crank is used to change the images. This backlit system uses a white light box with a diffusion panel to evenly spread the light across the image display portion of the canopy. Alternatively, as shown in FIG. 5, the projector 120 is used to project an image onto screen 145. Projector 120 can project the image directly onto the rear, inside surface of screen 145 or via a mirror. Alternatively, projector 120 can be mounted along the wall of the room outside of the canopy for projecting images directly onto the front of screen 145.

Another preferred embodiment for applying images to the image screen 145 employs rear projection technology currently used with televisions. The rear screen projection system includes a wide angle lens for projecting a received image onto the screen 145. When the screen is curved, the lens is ground in a predetermined manner so that the projected image will be evenly applied across the curved, translucent image screen 145. In an alternative embodiment, a plurality of lenses could be used as a system to provide single or multiple imaging effects.

In any of the disclosed embodiments or variations thereof, the image(s) can be provided by an analog or a digital signal source. Since the images are intended to have a therapeutic value to the patient, the person in charge of the therapy or protocol in which the patient is involved selects them.

Alternatively, the patient may be involved in selecting or directing the selection of the subject content for the images. However, the patient may not be able to communicate, whether verbally, or in an assisted manner, a directed personal choice. In these instances, the practitioner will be provided with numerous sets of still images, dynamic images (videos) and/or real time dynamic live video input material. The practitioner, nurse or other care provider may select subject material that suitable for conveyance of natural image settings that are appropriate for the patient's mental and physical condition.

The dynamic and real time images include digital or analog videos of friends and family members talking to the patient. They can also include videos of specific scenic areas or natural events that are of interest to the patient. For example, if the patient loves to climb mountains, the video may be the view of a pilot as he flies through a mountain range. Alternatively, the images could be individual digital photographs of different people or different locations.

No matter the type of image being provided, the system for controlling the image application to the screen 145 is well known in either or both the computer and television arts. For example, an APPLE laptop G3 computer with software such as JPEGView or MICROSOFT POWERPOINT can be used to deliver a sequence of images to the screen 145 for viewing by the patient. Alternatively, QUICKTIME could be used for providing digitally stored audio and/or video and for delivering streaming video and/or audio from the Internet. When a computer is not used to control the application of the images, video and/or audio, conventional audio-visual equipment could be utilized. This equipment can include a SONY SLV-N51 VHS player and/or a SONY DVD-s560D DVD player with a YAMAHA HTR-5240 receiver/amplifier. Any known speaker could be used with this system. One such speaker includes an ENERGY e:XL™ 15.

It is conceivable that video screens can be used in place of the image projection screen 145. In this case, the display screen would itself be an entire video monitor such as a cathode ray tube (CRT) or other types of known picture tubes. Also, new types of display devices, for example, flat panel display technology including color liquid crystal displays or plasma screens such as Plasmatron.RTM. by Sony Corporation, can also be used to display the comforting and relaxing images discussed above. In this embodiment, conventional digital projection technology is used to apply images to a plasma portion (screen 145) of the curved canopy 20. The digital image can be delivered from the image source, such as a computer, to the projection system using fiber optic cables or digital coaxial cables.

In another embodiment, the image can be a real time image received from a live feed. In this alternative embodiment, the images are received from a remote camera positioned at a location that is desired by the patient. The feed from this camera is projected onto screen 145 in real time by the system 100. The projection system 100 receives the live feed and projects it onto the screen 145 as is well known in the television production industry or by using the Internet and a rear projector 120. This embodiment permits the patient to see images from locations that they are familiar with and not able to visit. For example, a child could look in on his classroom at school or see his siblings and his dog moving around his house. This embodiment also allows a hospitalized mother or father to look in on the children at home that are not able to visit him/her in the hospital. In either instance, the projection system delivers real time images to the image screen 145 that will entertain, comfort and bring happiness to the patient confined to the hospital room.

The curved or flat image display screen 145 is shown in the figures as being positioned substantially horizontal or otherwise substantially parallel to the floor of the room. In a preferred embodiment, the image screen 145 is perpendicular to a viewer's line of sight as the viewer looks upward from the bed. This position is very convenient for patients forced to lie on their back. Also, when still images of the sky are shown, the overhead position showing an image of the sky can appear to be a skylight. However, in an alternative embodiment, the screen can be positioned at an angle to the horizontal. Any advantageous position which is suitable for projecting images onto the screen(s) in a rear-projection or other known type of projection system could be used. Additionally, a system that displays images at different screen angles to the viewer's line of sight can produce interesting visual effects. In an alternative embodiment, the screen 145 could be oriented so that it is parallel to the patient's line of sight and at an angle to the horizontal when the head of the bed has been raised. Well-known ways of mounting the screen for movement could be used. These include hydraulic systems and screw-thread system that can be controlled by any well-known control system so that the screen will move with the patient as the patient moves.

As discussed above, canopy 20 also includes a task lighting system 200. This lighting system 200 includes a plurality of lamps 201 that are secured within socket housings 220 in canopy 20. The lighting system 200 provides different lighting schemes within the room for performing different tasks, such as patient examination and general illumination. Each lamp 201 is controlled to cooperate with one or more of the other lamps 201 to provide specific, predetermined task lighting and ambient/general lighting within the room. This is true for all the lamps 201 except for the individual lamp that is closest to the patient's chart. This lamp can be individually operated without the other lamps 201. As a result, the chart can be read at 3:00 AM without the entire room being illuminated and the sleeping patient being disturbed.

In a preferred embodiment, the lamps 201 are well known incandescent lamps that are secured in the socket housings 220 and positioned at predetermined locations within the canopy 20 so that they can provide the desired task lighting schemes. In an alternative embodiment, the lamps 201 include halogen sources 205, such as MR-16 lamps, positioned within the canopy 20. No matter the type of bulb, the lamps 201 of lighting system 200 are arranged so that different tasks can be accomplished by illuminating only some of the lamps 201. For example, one or more of the lamps 201 can be operated independent of the other lamps 201 to provide reading light at the head of the bed. Also, one or more lamps 201 can be used as a night light or an emergency medical lighting system. As shown in FIG. 2, the lamps 201 that are also designated as 202 are focused on the patient's bed and create an examination lighting scheme within the room. These lamps 202 illuminate the patient so that a doctor or nurse can perform a necessary examination without having to turn on all of the lights (lamps 201) within the room. All of the above-discussed lamps 201 can be connected to a programmable lighting control system that allows the lamps 201 to be automatically dimmed or illuminated.

These lamps 201 include focusing lenses 203 that are flush with the outer surface of the canopy for changing the diffusion of their emitted light. These lenses 203 can be manually or automatically adjusted to make the emitted column of light broader or, alternatively, narrower and sharper.

A computer including a microprocessor controls the operation of the individual lamps 201. The microprocessor operates a prescribed program for accomplishing one or more predetermined lighting sequences in response to a specific input. The programmed sequence(s) can be automatically and manually stopped. An appropriate input includes depressing a button or otherwise activating a switch associated with the desired lighting task. An alternative input includes typing the code for a predetermined lighting scheme into a keypad in order to activate the scheme. For example, when a code relating to the examination lighting scheme is keyed into a number pad, the microprocessor initiates a predetermined lighting sequence. The examination lighting sequence can include the sequential illumination of some or all of the lamps 201. Alternatively, the lighting scheme could include the simultaneous illumination of one or more of the lamps 201. For example, when the code for the examination lighting scheme is inputted, the simultaneous illumination of the head, mid section and foot of the patient's bed by three lamp sets of lamps 202 could occur. Each lamp 202 may form a portion of more than one of the lamp sets. In this instance, if the light is moved down the bed and away from the patient's head, certain lamps 202 will remain illuminated, certain lamps 202 may become illuminated and certain lamps 202 will be turned off. Alternatively, each lamp 202 may only be assigned to a single set of lamps within the lighting scheme.

The microprocessor can also automatically change between different lighting schemes without being prompted. For example, the microprocessor can automatically change between the examination illumination scheme, a general ambient illumination scheme, a therapy illumination scheme, an emergency illumination scheme, a pre-dawn/pre-sunrise illumination scheme and a nighttime/sleep illumination scheme. Alternatively, these changes can be performed manually. In the automatically changing embodiment, the transition between the tasks would be preprogrammed so that the person working with the patient would not have to push a button, throw a switch or input a code each time she completes a task or wants to begin a new task. Instead, a predetermined amount of time would be allotted for the completion of each task. At the end of each time period, the lighting would be automatically cycled to the next task and the appropriate lamps 201 illuminated. Of course, a manual or remote control switch could be provided for overriding the program and allowing the attendant to manually control the lighting scheme. For an example, the general ambient lighting scheme may be timed for 3 hours and then the nighttime/sleeping scheme would be set for 8 hours. The manual override would permit the attendant to interrupt the nighttime/sleeping scheme if activation of the examination lighting scheme is necessary. One such controller that can be used to perform the above discussed lighting schemes includes those of the Lutron GRAFIK Eye 3000 series available from LUTRON® Electronics Inc. However, other well known light controllers could also be used so that the different lighting schemes are automatically or manually provided in the room at different times of the day and night.

Figure 4:
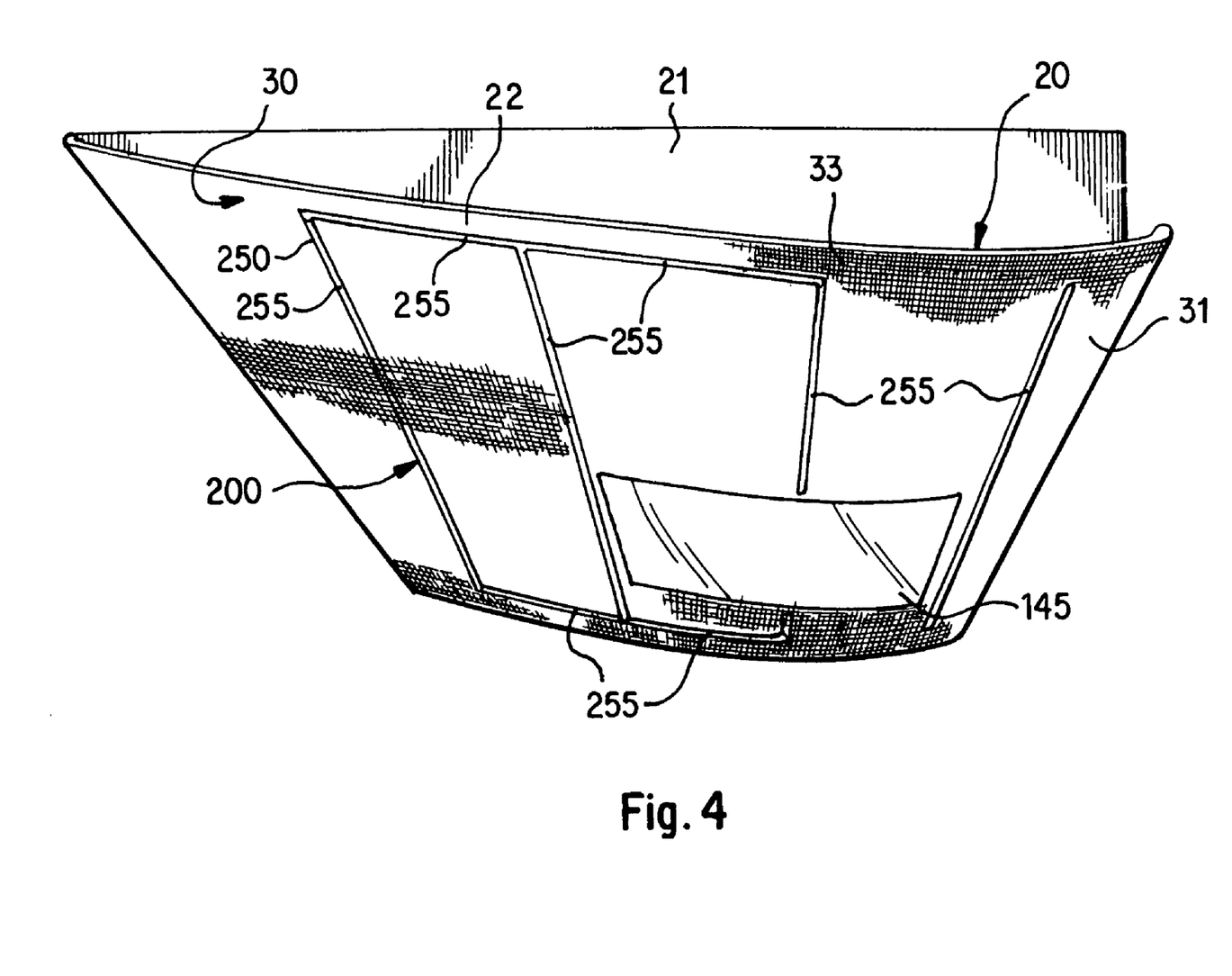
FIG. 4 is a side perspective view of another embodiment of the overhead system according to the present invention.

As shown in FIG. 4, another embodiment of the lighting system 200 uses rows of fiber optic cables 255 secured within very narrow slots 250 in the canopy 20. These rows 250 of fiber optic lights 260 include multiple oculars covered by a fabric. Each fiber optic cable 255 provides point source lighting that is diffused by the covering fabric to wash the room with light without causing patient discomfort.

The lighting system 200 also includes the artificial light source(s) 16 provided to supplement the natural light source when a sufficient amount of natural light is not available. For instance, the light source 16 could be used at dusk or at night to indirectly light the room. Light source(s) 16 include incandescent or florescent lamps positioned within canopy 20 so that the emitted light will diffuse off surface 91 in the direction of canopy 20. The exact position of the light source(s) 16 will depend on where the light is intended to contact canopy 20. For example, the light sources 16 may be positioned along the surface of the canopy 20 closest to the windows.

While the above description contains many specifics, these should not be construed as limitations on the scope of the invention, but rather as an exemplification of one preferred embodiment thereof. Other variations are possible. Accordingly, the scope of the present invention should be determined not by the embodiments illustrated above, but by the appended claims and their legal equivalents.

The invention claimed is:

1. A system for comforting a person within a room, said system comprising:
    a canopy structure for extending away from a ceiling and above the person, said canopy structure having a lower outer surface for facing a room floor, said lower outer surface including at least one light diffusion section that is shaped to diffuse light away from said canopy structure and into the room, said at least one light diffusion section of said lower outer surface being curved upward from a location spaced inwardly from a boundary of said lower outer surface to a first end of said canopy structure; wherein the curved configuration is formed by a single radius of curvature having an end at the location spaced from an edge of the lower outer surface; wherein the location has the greatest vertical distance measured from the first end than the rest of the lower outer surface;
    a lighting system including at least one lighting source is positioned within said canopy structure, said at least one lighting source being capable of projecting light in a direction away from said canopy structure for illuminating a room;
    an image display screen extending along a portion of said canopy structure; and
    an image source for providing images on said image display screen so that the images can be viewed by the person.

2. The system according to claim 1 further comprising a light diffusion shelf proximate a light source spaced from the lower outer surface of the canopy structure.

3. The light system according to claim 2 wherein said light diffusion shelf includes a light reflective covering.

4. The light system according to claim 3 wherein said light reflective coating includes a reflective paint.

5. The system according to claim 2 wherein said light source includes an artificial light source positioned proximate the canopy structure.

6. The system according to claim 5 wherein said artificial light source includes at least one light source positioned proximate an end of the canopy structure proximate said light diffusion shelf.

7. The system according to claim 1 wherein said at least one diffusion section comprises first and second light diffusing sections, said first light diffusing section having a first end at said first end of said canopy structure for being spaced a first distance from the ceiling and said second light diffusing section having a portion for being spaced a second distance from the ceiling, said second distance being greater than said first distance.

8. The system according to claim 7 wherein said second light diffusing section extends substantially parallel to the image display screen between a position along the length of the canopy structure and a second end of the canopy structure.

9. The system according to claim 7 further including a light diffusing area that extends between said first and second light diffusing sections, said light diffusing area extending substantially parallel to the image display screen.

10. The system according to claim 1 wherein said at least one lighting source comprises a plurality of spaced lighting sources located within said canopy structure.

11. The system according to claim 10 wherein said lighting sources include a plurality of lamps positioned along the lower outer surface of the canopy.

12. The system according to claim 11 wherein said lamps each include a focusing lens.

13. The system according to claim 10 wherein said at least one lighting source includes at least one row of a fiber optic cable.

14. The system according to claim 13 wherein said at least one lighting source includes a plurality of fiber optic cables secured within said canopy structure.

15. The system according to claim 1 wherein said image display screen includes an outer surface covered by a material which permits an image from the image source to be displayed.

16. The system according to claim 15 wherein said material includes a coated fabric.

17. The system according to claim 1 wherein a portion of said lower outer surface of the canopy structure includes a light deflecting cover.

18. The system according to claim 1 wherein said image source includes a system for projecting images on the image display screen.

19. The system according to claim 18 wherein said system for projecting images includes a rear projection system that is mounted within said canopy structure.

20. The system according to claim 18 wherein said system for projecting images includes a projector for displaying still images on said image display screen.

21. The system according to claim 20 wherein said projector is located within the canopy structure.

22. The system according to claim 20 wherein said projector is located outside of said canopy structure.

23. The system according to claim 18 wherein said image source comprises a digital image source.

24. The system according to claim 23 wherein said digital image source comprises a digital camera.

25. The system according to claim 23 wherein said digital image source comprises a digital video disk player.

26. The system according to claim 18 wherein said image source comprises an analog image source.

27. The system according to claim 1 further including a plurality of controls that permit a user to create a plurality of predetermined task lighting sequences.

28. A system for providing biosychronized therapy to an individual, said system comprising:

a light diffusing member for securing to a ceiling, said member comprising a lower surface shaped having at least a first light diffusing section for diffusing light into a room away from a source of the light, said first light diffusing section being curved upward from a location spaced from an edge of said lower surface to a first end of said light diffusing member nearest to the ceiling; wherein the location space from an edge of the lower surface shape has the greatest vertical distance measured from the first end than the rest of the lower surface shape;

light emitting members positioned along an outer lower surface of the light diffusing member for providing light in a room in addition to the light from the source of light;

an image delivery system; and an image display member positioned relative to said image delivery system so that images delivered by said delivery system can be seen on said image display member.

29. A method for providing bio-synchronized therapy to an individual within a room, said method comprising the steps of:

diffusing light from a light source deep into the room occupied by the individual in a direction away from the light source by directing light off a member comprising a lower surface having a light diffusing section that is curved upward from a location spaced from an edge of said lower surface to a first end of said light diffusing member collectively defining a curved configuration; wherein a horizontal length of the curved configuration is about two-thirds of the length of the member; and providing images on an overhead canopy that comfort and relax the individual.

30. The method of claim 29 further including a step of providing task lighting within the room so that predetermined light sequences can be achieved.

31. The method of claim 30 wherein said diffusing light step includes diffusing natural light into the room using said overhead canopy extending from a ceiling.

32. The method of claim 30 wherein said diffusing light step includes diffusing artificial light into the room using said overhead canopy extending from a ceiling.

33. The method of claim 32 further comprising the step of providing artificial light from a source positioned proximate an end of said overhead canopy.

34. The method of claim 29 wherein said providing images step includes providing predetermined images that have been found to comfort and relax the individual.

35. The method of claim 29 further including the step of providing artificial lighting within the room by activating light sources within said overhead canopy.

* * * * *